(12) United States Patent
Lee et al.

(10) Patent No.: US 11,497,703 B2
(45) Date of Patent: *Nov. 15, 2022

(54) PACKAGED HAIR CARE COMPOSITION

(71) Applicant: The Procter & Gamble Company, Cincinnati, OH (US)

(72) Inventors: Martin Chang Shou Lee, Singapore (SG); Yan Wang, Singapore (SG)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/005,416

(22) Filed: Aug. 28, 2020

(65) Prior Publication Data

US 2021/0059926 A1 Mar. 4, 2021

Related U.S. Application Data

(60) Provisional application No. 62/893,951, filed on Aug. 30, 2019.

(51) Int. Cl.
*A61Q 5/12* (2006.01)
*A61K 8/891* (2006.01)

(52) U.S. Cl.
CPC ............... *A61K 8/891* (2013.01); *A61Q 5/12* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 3,866,800 A | 2/1975 | Schmitt | |
| 5,538,720 A | 7/1996 | Jendryssek-pfaff | |
| 6,082,588 A | 7/2000 | Markey | |
| 6,129,243 A * | 10/2000 | Pal | B65D 35/22 |
| | | | 222/105 |
| 6,274,128 B1 | 8/2001 | Bergmann | |
| 6,877,638 B2 | 4/2005 | Chan | |
| 8,052,016 B2 * | 11/2011 | Wang | B65D 35/22 |
| | | | 222/485 |
| 8,413,845 B1 | 4/2013 | Duncan | |
| 10,335,818 B2 | 7/2019 | Pointel | |
| 2004/0028711 A1 | 2/2004 | Uchida | |
| 2007/0041929 A1 | 2/2007 | Torgerson | |
| 2007/0095702 A1 | 5/2007 | Park et al. | |
| 2007/0119861 A1 | 5/2007 | Bhagwat | |
| 2007/0196403 A1 | 8/2007 | Uchida et al. | |
| 2008/0128423 A1 | 6/2008 | Rick | |
| 2008/0128425 A1 | 6/2008 | Rick et al. | |
| 2008/0128426 A1 | 6/2008 | Rick | |
| 2009/0152294 A1 | 6/2009 | Mizell | |
| 2011/0259914 A1* | 10/2011 | Lee | B29C 65/368 |
| | | | 156/251 |
| 2014/0230842 A1 | 8/2014 | Parris | |
| 2014/0263448 A1* | 9/2014 | Erskine-Smith | B65D 81/3288 |
| | | | 222/143 |
| 2014/0290685 A1 | 10/2014 | Battermann | |
| 2014/0335040 A1 | 11/2014 | Yu et al. | |
| 2015/0093347 A1 | 4/2015 | Uehara et al. | |
| 2015/0157544 A1 | 6/2015 | Briggs et al. | |
| 2015/0208859 A1 | 7/2015 | Wang | |
| 2015/0216786 A1 | 8/2015 | Yu et al. | |
| 2016/0374919 A1 | 12/2016 | Hakozaki | |
| 2017/0246093 A1 | 8/2017 | Horne | |
| 2018/0360725 A1 | 12/2018 | Hoffmann et al. | |
| 2020/0000689 A1 | 1/2020 | Zukowski | |
| 2020/0093731 A1 | 3/2020 | Brac De La Perriere et al. | |
| 2021/0008578 A1 | 1/2021 | Bartolucci et al. | |
| 2021/0009336 A1 | 1/2021 | Bartolucci et al. | |
| 2021/0059925 A1 | 3/2021 | Lee et al. | |
| 2021/0069081 A1 | 3/2021 | Hiruma et al. | |

(Continued)

FOREIGN PATENT DOCUMENTS

EP 0586929 A1 3/1994
EP 1516613 A1 3/2005

(Continued)

OTHER PUBLICATIONS

PCT Search Report and Written Opinion for PCT/US2020/070469 dated Dec. 18, 2020, 13 pages.
Database GNPD [Online], Mintel, Anonymous, "Cleansing Oil Creme Duo", XP055758338, Database accession No. 4686899, dated May 9, 2017, pp. 1-3.
U.S. Appl. No. 17/510,478, filed Oct. 26, 2021, to Martin Chang Shou Lee et al.
U.S. Appl. No. 17/005,411, filed Aug. 28, 2020, Lee et al.
U.S. Appl. No. 16/924,264, filed Jul. 9, 2020, Bartolucci et al.
Database GNPD [Online] Mintel; anonymous: "Heat Mask", dated Apr. 25, 2017 (Apr. 25, 2017), pp. 3, XP055894037, Database accession No. 4760985.

(Continued)

*Primary Examiner* — Jyothsna A Venkat
(74) *Attorney, Agent, or Firm* — Kathleen Y Carter

(57) ABSTRACT

A packaged hair care composition comprising a first composition and a second composition, wherein the first and second compositions are kept in separate packaging chambers until dispensed. The first composition comprises a cationic polymer; and an aqueous carrier and has a G' value of about 160 to about 410; and the second composition comprises: a cationic surfactant; a high melting point fatty compound; and an aqueous carrier and has a G' value of from about 600 Pa to about 3000 Pa. The package comprises an outer tube body having an exterior layer and an outer tube interior chamber; and an inner tube having an exterior layer and an inner tube body having an inner tube interior chamber; a dispensing orifice wherein a portion of the dispensing orifice is in communication with the outer tube interior chamber, and a portion of the dispensing orifice is in communication with the inner tube interior chamber.

23 Claims, 5 Drawing Sheets

(56) References Cited

U.S. PATENT DOCUMENTS

| | | |
|---|---|---|
| 2021/0128422 A1 | 5/2021 | Zukowski et al. |
| 2021/0128436 A1 | 5/2021 | Zukowski et al. |
| 2021/0137244 A1 | 5/2021 | Zukowski et al. |

FOREIGN PATENT DOCUMENTS

| | | |
|---|---|---|
| EP | 1787634 A1 | 5/2007 |
| KR | 20200122083 A | 10/2020 |
| WO | 0219977 A1 | 3/2002 |
| WO | 2004035016 A1 | 4/2004 |
| WO | 2014124066 A1 | 8/2014 |
| WO | 2015024078 A1 | 2/2015 |
| WO | 2017057784 A1 | 4/2017 |
| WO | 2017115827 A1 | 7/2017 |
| WO | 2017116552 A1 | 7/2017 |

OTHER PUBLICATIONS

Database GNPD [Online] Mintel; anonymous: "Warming Express Mask", dated Jul. 10, 2018 (Jul. 10, 2018), pp. 3, XP055894031, Database accession No. 5825017.
All final and non-final office actions for U.S. Appl. No. 16/224,269 (P&G Case AA1360).
All final and non-final office actions for U.S. Appl. No. 16/924,264 (P&G Case AA1358).
All final and non-final office actions for U.S. Appl. No. 17/005,411 (P&G Case AA1364).
All Office Actions; U.S. Appl. No. 17/005,411, filed Aug. 28, 2020.

\* cited by examiner

PACKAGED HAIR CARE COMPOSITION

FIELD OF THE INVENTION

Dispensing of a multi-phase hair care composition comprising a first composition and a second composition, wherein the first and second compositions are kept separate from one another until use, and wherein the product has a consistent dispense ratio and also has less residue at the end of the tube lifespan.

BACKGROUND OF THE INVENTION

A variety of approaches have been developed to dispense a multi-phase product. A common method is a multi-chamber tube or bottle. However, typical tubes or bottles have difficulty dispensing the phases in a predictable way. Additionally, often there is residue left in the tube, which is not desired by the consumer. The consumer desires hair care compositions that dispense in a visually appealing manner, additionally the consumer desires to dispense product uniformly and completely from the tube.

Therefore, there is still a need for providing a multi-phase hair care composition that dispenses in a predictable pattern and/or ratio and further dispenses such that there is little residue remaining in the tube at the end of the tube lifespan.

SUMMARY OF THE INVENTION

A packaged hair care composition comprising a hair care composition comprising: a first composition and a second composition, wherein the first and second compositions are kept separate from one another until dispensed, wherein the first composition comprises: a cationic polymer; and an aqueous carrier and has a G' value of about 160 Pa to about 410 Pa; and wherein the second composition comprises: a cationic surfactant; a high melting point fatty compound; and an aqueous carrier and has a G' value of from about 600 Pa to about 3000 Pa a package comprising: an outer tube body having an exterior layer wherein the outer tube exterior layer has a stiffness of from about 3.0 N to about 9.5 N and a thickness of from about 300 µm to about 600 µm and an outer tube interior chamber; and an inner tube having an exterior layer wherein the interior tube exterior layer has a stiffness of from about 2.9N to about 9.5N and a thickness of from about 200 µm to about 600 µm and an inner tube body having an inner tube interior chamber; a dispensing orifice wherein a portion of the dispensing orifice is in communication with the outer tube interior chamber, and a portion of the dispensing orifice is in communication with the inner tube interior chamber; wherein the first composition is located in the outer tube interior chamber, and the second composition is located in the inner tube interior chamber.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated. The weight average molecular weight may be measured by gel permeation chromatography.

"QS" means sufficient quantity for 100%.

Packaged Hair Care Composition

The hair care composition comprises a first composition and a second composition, wherein the first and second compositions are kept separate from one another until dispensed. The first composition comprises: a cationic polymer; and an aqueous carrier, and the second composition comprises a cationic surfactant; a high melting point fatty compound; and an aqueous carrier. The first composition and/or the second composition may further comprise a silicone compound.

Figure 1A:
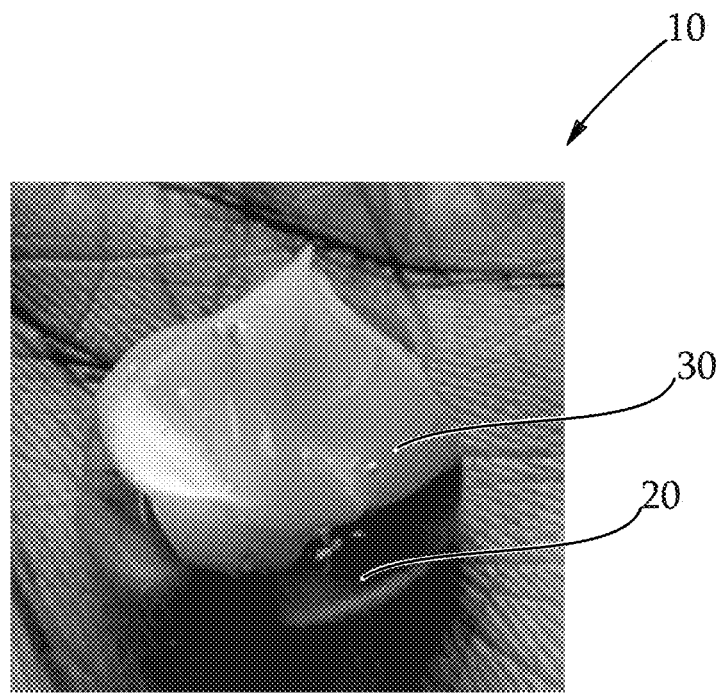
FIGS. 1A and 1B are dispensed hair care composition.
Figure 1B:
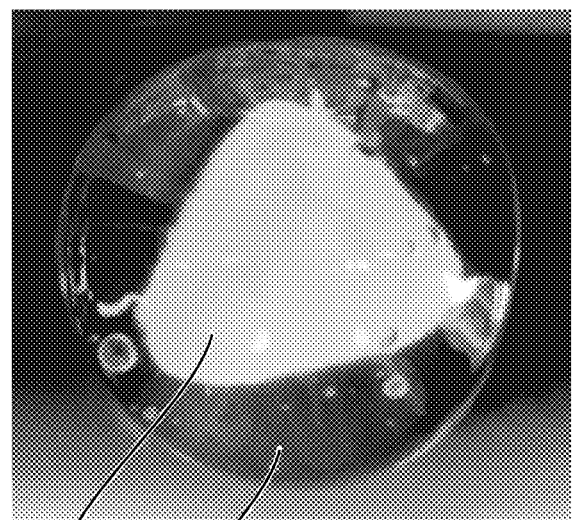

Although kept separate until dispensing, the first and second composition and the second composition are put into contact upon dispensing. The dispensed hair care composition G' ratio of first composition and the second composition is from about 0.10 to about 0.40, from about 0.11 to about 0.35, and from about 0.13 to about 0.30. FIGS. 1A and 1B show the dispensed hair care composition 10 comprising the first composition 20, and the second composition 30. When a package as described herein is used to dispense the first and second compositions described herein, the two compositions dispense at the same time in a consistent dispensing ratio. The product can be visible even after dispensed as two separate phases. Additionally, the product can dispense such that there is minimal residue (from about 0 Wt. % to about 12.5 Wt. %, alternatively less than 12.5 Wt. %) remaining at the end of the tube lifespan as compared to existing tubes. Residue is the % of product remaining in the package after the consumer has dispensed all product that will dispense through normal use.

| | First composition | Second composition | Residue |
|---|---|---|---|
| Example 1 | 90 g | 110 g | <12.5% |
| Comparative Exp A | 100 g | 100 g | 15% |

|  | Example 1 | Example 2 | Comparative A |
|---|---|---|---|
| G' second composition (inner composition) | 1568 | 1568 | 2089 |
| G' First Composition (outer composition) | 226 | 226 | 199 |
| G' ratio first/second composition | 0.14 | 0.14 | 0.10 |
| Average dispense ratio | 0.73 | 0.43 | 2.36 |
| Average dispense ratio std. | 0.07 | 0.07 | 2.26 |

First Composition

The first composition comprises: a cationic polymer; and an aqueous carrier. A suitable cationic polymer includes, but is not limited to, polyquaternium-37.

The first composition can be substantially free of high melting point fatty compound. "The first composition being substantially free of high melting point fatty compounds" means that: the composition is free of high melting point fatty compounds; or, if the composition contains high melting point fatty compounds, the level of such high melting point fatty compounds is very low. A total level of such high melting point fatty compounds in the first composition, if included, is 1% or less, 0.5% or less, and 0.1% or less by weight of the composition. The total level of such high melting point fatty compounds in the first composition can be 0% by weight of the composition.

The first composition can be substantially free of cationic surfactant. "The first composition being substantially free of cationic surfactants" means that: the composition is free of cationic surfactants; or, if the composition contains cationic surfactants, the level of such cationic surfactants is very low. A total level of such cationic surfactants in the first composition, if included, is 0.3% or less, 0.2% or less, and 0.1% or less by weight of the composition. The total level of such cationic surfactants in the first composition can be 0% by weight of the composition.

The first composition can have a G' value of from about 160 Pa to about 410 Pa, from about 175 Pa to about 390 Pa, from about 190 Pa to about 370 Pa.

Second Composition

The second composition comprises: a cationic surfactant; a high melting point fatty compound; and an aqueous carrier. The second composition can further comprises a silicone compound. Suitable silicone compound used herein conforms to the general formula:

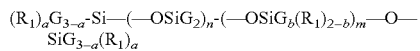

wherein G is hydrogen, phenyl, hydroxy, or $C_1$-$C_8$ alkyl, preferably methyl; a is 0 or an integer having a value from 1 to 3; b is 0, 1 or 2; n is a number from 0 to 1,999; m is an integer from 0 to 1,999; the sum of n and m is a number from 1 to 2,000; a and m are not both 0; $R_1$ is a monovalent radical conforming to the general formula $C_qH_{2q}L$, wherein q is an integer having a value from 2 to 8 and L is selected from the following groups: —N($R_2$)CH$_2$—CH$_2$—N($R_2$)$_2$; —N($R_2$)$_2$; —N($R_2$)$_3$A$^-$; —N($R_2$)CH$_2$—CH$_2$—NR$_2$H$_2$A$^-$; wherein $R_2$ is hydrogen, phenyl, benzyl, or a saturated hydrocarbon radical; A$^-$ is a halide ion. The silicone compounds can include those conforming to the above formula, wherein m=0.

The second composition can have a G' value of from about 600 Pa to about 3000 Pa, from about 650 Pa to about 2700 Pa, from about 700 Pa to about 2300 Pa.

Cationic Polymer

The first composition can comprise a cationic polymer. The cationic polymer can be contained in the composition at a level of from about 0.5% to about 3.0%, from about 0.8% to about 2.0%, from about 1.2% to about 1.5% by weight of the composition.

The cationic polymer useful herein is water soluble, and can be natural, derived from natural, and/or synthetic.

The cationic polymer useful herein is that having a cationic charge density of, from about 0.1 meq/g, from about 0.5 meq/g, from about 1.0 meq/g, and to about 13.0 meq/g.

The cationic polymer useful herein is that having a molecular weight of, about 800 g/mol or more, 1,000 g/mol or more, 1,200 g/mol or more. The molecular weight is up to about 5,000,000 g/mol, up to about 4,600,000 g/mol, to about 4,300,000 g/mol, up to about 4,000,000 g/mol.

Cationic polymers useful herein include, for example, are Polyquaternium-4, Polyquaternium-6, Polyquaternium-7, Polyquaternium-10, Polyquaternium-11, Polyquaternium-37, cationic cellulose polymers, cationic guar polymers and combinations thereof.

Cationic Surfactant

The second composition can comprise a cationic surfactant. The cationic surfactant can be included in the composition at a level of from about 1.0%, from about 1.5%, from about 2.0%, still from about 3.0%, and to about 25%, to about 10%, to about 8.0%, to about 6.0% by weight of the composition by weight of the composition.

Cationic surfactant useful herein can be one cationic surfactant or a mixture of two or more cationic surfactants. The cationic surfactant can be selected from the group consisting of: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt.

Mono-long alkyl amine useful herein are those having one long alkyl chain of from 12 to 30 carbon atoms, from 16 to 24 carbon atoms, from 18 to 22 alkyl group. Mono-long alkyl amines useful herein also include mono-long alkyl amidoamines. Primary, secondary, and tertiary fatty amines are useful.

Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethyl amine, behenamidopropyldimethyl amine, behenamidopropyldiethylamine, behenamidoethyldiethyl amine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Suitable amines are disclosed in U.S. Pat. No. 4,275,055, Nachtigal, et al.

These amines are used in combination with acids such as ℓ-glutamic acid, lactic acid, hydrochloric acid, malic acid, succinic acid, acetic acid, fumaric acid, tartaric acid, citric acid, ℓ-glutamic hydrochloride, maleic acid, and mixtures thereof; ℓ-glutamic acid, lactic acid, citric acid, at a molar ratio of the amine to the acid of from about 1:0.3 to about 1:2, from about 1:0.4 to about 1:1.

Suitable mono-long alkyl quaternized ammonium salt cationic surfactants include, but are not limited to, behenyl trimethyl ammonium salt; stearyl trimethyl ammonium salt; cetyl trimethyl ammonium salt; and hydrogenated tallow alkyl trimethyl ammonium salt, and any combination thereof.

Suitable di-long alkyl cationic surfactants include, but are not limited to, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride and any combination thereof.

High Melting Point Fatty Compound

The second composition comprises a high melting point fatty compound. The high melting point fatty compound can be included in the composition at a level of from about 2.5%, from about 3.0%, from about 4.0%, from about 5.0%, and to about 30%, to about 10%, to about 8.0% by weight of the composition.

The high melting point fatty compound useful herein can have a melting point of 25° C. or higher, 40° C. or higher, 45° C. or higher, 50° C. or higher, in view of stability of the emulsion especially the gel matrix. The melting point can be up to about 90° C., up to about 80° C., up to about 70° C., up to about 65° C., in view of easier manufacturing and easier emulsification. The high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifth Edition, 1993, and CTFA Cosmetic Ingredient Handbook, Second Edition, 1992.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof.

The fatty alcohol can be a mixture of cetyl alcohol and stearyl alcohol.

Generally, in the mixture, the weight ratio of cetyl alcohol to stearyl alcohol is from about 1:9 to 9:1, from about 1:4 to about 4:1, from about 1:2.3 to about 1.5:1.

When using higher level of total cationic surfactant and high melting point fatty compounds, the mixture has the weight ratio of cetyl alcohol to stearyl alcohol of from about 1:1 to about 4:1, from about 1:1 to about 2:1, from about 1.2:1 to about 2:1.

Aqueous Carrier

The compositions of the can comprise an aqueous carrier. The level and species of the carrier are selected according to the compatibility with other components, and other desired characteristic of the product.

Suitable aqueous carriers include water and water solutions of lower alkyl alcohols. The lower alkyl alcohols useful herein are monohydric alcohols having 1 to 6 carbons, alternatively ethanol and isopropanol.

The aqueous carrier can be substantially water. Deionized water is suitable. Water from natural sources including mineral cations can also be used, depending on the desired characteristic of the product. The first compositions can comprise from about 80% to about 99%, from about 85% to about 99%, from about 90% to about 99%, from about 95% to about 98% aqueous carrier. The second compositions can comprise from about 40% to about 99%, from about 50% to about 95%, from about 70% to about 90%, and from about 80% to about 90% aqueous carrier.

Gel Matrix

A gel matrix can be formed by the cationic surfactant, the high melting point fatty compound, and an aqueous carrier in the second composition. The gel matrix is suitable for providing various conditioning benefits, such as slippery feel during the application to wet hair and softness and moisturized feel on dry hair.

When the gel matrix is formed, the cationic surfactant and the high melting point fatty compound are contained at a level such that the weight ratio of the cationic surfactant to the high melting point fatty compound is in the range of, from about 1:1 to about 1:10, from about 1:1.5 to about 1:7, from about 1:2 to about 1:6, in view of providing conditioning benefits.

Silicone Compound

The compositions may further contain a silicone compound. The silicone compounds herein can be used at levels by weight of the composition of from about 0.1% to about 20%, from about 0.5% to about 10%, from about 1% to about 8%.

The silicone compounds have an average particle size of from about 1 microns to about 50 microns, in the composition.

Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Suitable polyalkyl siloxanes include, for example, polydimethylsiloxane, polydiethylsiloxane, and polymethylphenylsiloxane.

The silicone compound can conform to the general formula:

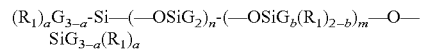

$(R_1)_a G_{3-a}\text{-Si}-(-OSiG_2)_n-(-OSiG_b(R_1)_{2-b})_m-O-SiG_{3-a}(R_1)_a$ wherein G is hydrogen, phenyl, hydroxy, or $C_1$-$C_8$ alkyl, preferably methyl; a is 0 or an integer having a value from 1 to 3; b is 0, 1 or 2; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: $-N(R_2)CH_2-CH_2-N(R_2)_2$; $-N(R_2)_2$; $-N(R_2)_3 A^-$; $-N(R_2)CH_2-CH_2-NR_2H_2A^-$; wherein $R_2$ is hydrogen, phenyl, benzyl, or a saturated hydrocarbon radical; $A^-$ is a halide ion.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Suitable solvents include, but are not limited to, are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, from about 20 to about 10,000 centistokes at 25° C. Suitable solvents include, but are not limited to, non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of from about 1,000 mPa·s to about 100,000 mPa·s, and from about 5,000 mPa·s to about 50,000 mPa·s.

Other suitable alkylamino substituted silicone compounds include those having alkylamino substitutions as pendant groups of a silicone backbone, including those known as "amodimethicone". Commercially available amodimethicones useful herein include, for example, BY16-872 available from Dow Corning.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Additional Components

The composition may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben phenoxyethanol, Sodium Benzoate, Symdiol68 (1,2-Hexanediol and Caprylyl Glycol), SymSaveH (Hydroxyacetophenone), imidazolidinyl urea and combinations thereof; pH adjusting agents, such as citric acid, sodium citrate, succinic acid, phosphoric acid, sodium hydroxide, sodium carbonate; coloring agents, such as any of the FD&C or D&C dyes; perfumes; ultraviolet and infrared screening and absorbing agents such as benzophenones; and antidandruff agents such as zinc pyrithione; non-ionic surfactant such as mono-9-octadecanoate poly (oxy-1,2-ethanediyl) supplied as, for example, Tween 20; and buffer such as aminomethyl propanol, and combinations thereof.

Product Forms

The compositions can be in the form of rinse-off products or leave-on products, and can be formulated in a wide variety of product forms, including but not limited to creams, gels, emulsions, mousses and sprays. The compositions are especially suitable for hair conditioners especially leave-on, leave-in, and/or no-rinse hair conditioners. Leave-on and leave-in hair conditioners are generally used on dry, semi-wet, and/or wet hair without rinsing out the conditioner. By no-rinse hair conditioners, what is meant herein is a hair conditioner used on semi-wet to wet hair after shampooing, without rinsing out the conditioner.

Package

As used herein "The first and second compositions are kept separated from one another" means, for example: a package comprising two chambers, wherein the first composition is contained in a first chamber and the second composition is contained in a separate second chamber. Such packages can be shaped as a tube, pump, bottle or upside-down bottle, and blister pack.

Figure 2:
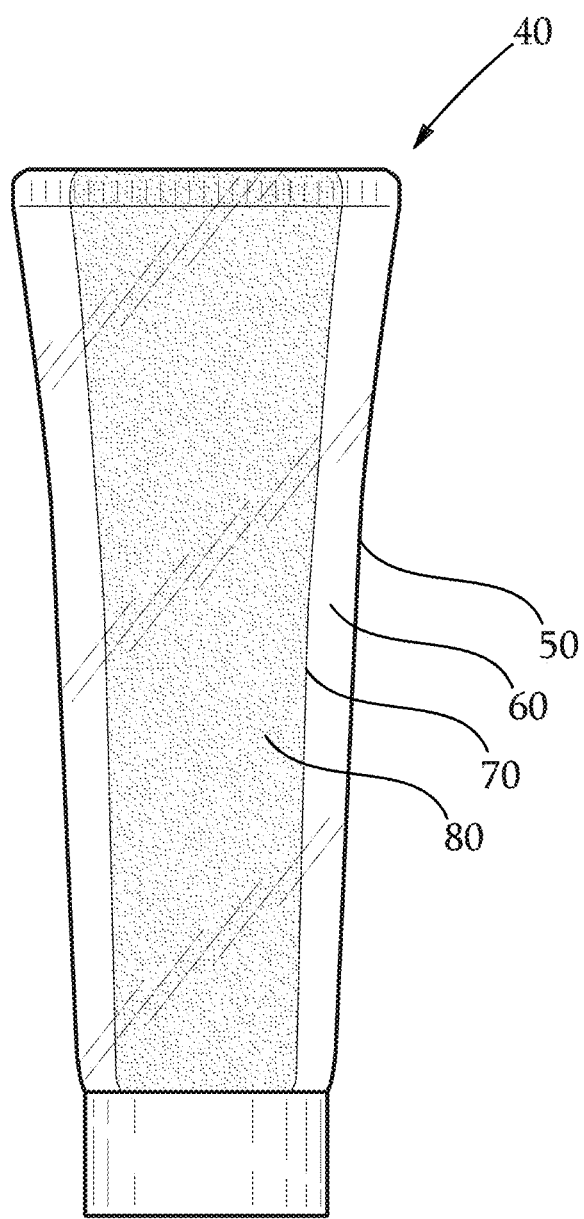
FIG. 2 is a view of the packaged hair care composition and the tube in tube package.
Figure 3:
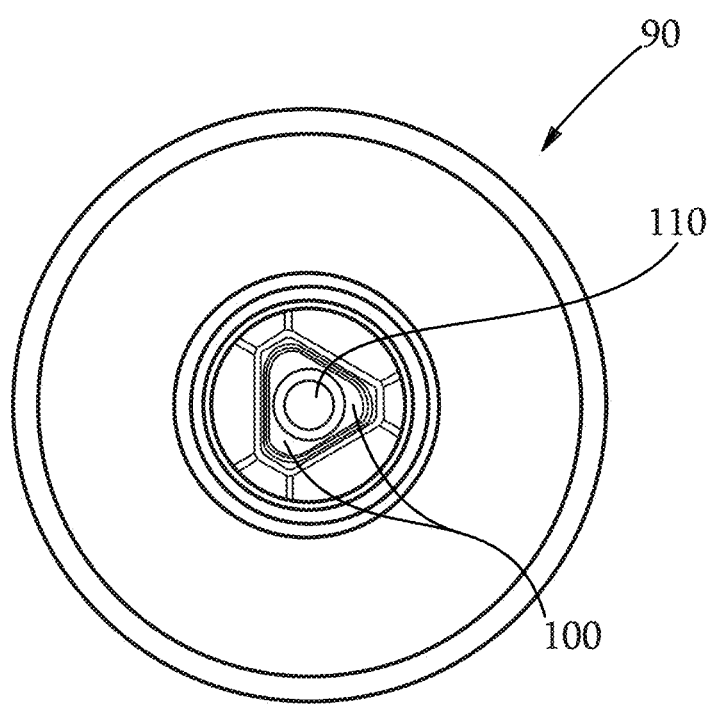
FIG. 3 is a view of the dispensing orifice.

The package 40 is shown in FIG. 2. The package comprises an outer tube body having an exterior layer 50, wherein the outer tube exterior layer has a stiffness of from about 3.0 N to about 9.5 N, from about 3.0 N to about 5.5 N, from about 3.2 N to about 4.0 N and a thickness of from about 300 μm to about 600 μm, from about 300 μm to about 500 μm, and from about 300 μm to about 400 μm. The outer tube body further comprises an outer tube interior chamber 60. The package also comprises an inner tube having an exterior layer 70, wherein the inner tube exterior layer has a stiffness of from about 2.9 N to about 9.5 N, from about 3.0 N to about 6.0 N, and from about 4.0 N to about 5.0 N and a thickness of from about 200 μm to about 600 μm from about 300 μm to about 500 μm, from about 400 μm to about 500 μm. The inner tube body further comprises an inner tube interior chamber 80. The package further comprises a dispensing orifice 90. A portion 100 of the dispensing orifice is in communication with the outer tube interior chamber, and a portion 110 of the dispensing orifice is in communication with the inner tube interior chamber. During dispensing for use the composition flows from the outer and inner interior chambers through the dispensing orifice. The stiffness ratio of the exterior layer of the outer tube, to the exterior layer of the inner tube is from about 0.35 to about 1.2, from about 0.6 to about 1.2 and from about 0.7 to about 1.0.

The outer tube exterior layer can comprise a material selected from the group consisting of plastic laminate, metallized laminate, aluminum laminate, high density polypropylene, low density polypropylene, polypropylene, and combinations thereof. The inner tube exterior layer comprises a material selected from the group consisting of plastic laminate, metallized laminate, aluminum laminate, high density polypropylene, low density polypropylene, polypropylene, and combinations thereof. The inner tube exterior layer can comprise about 50% high density polypropylene and 50% low density polypropylene. Additionally the outer tube exterior layer can comprise plastic barrier layer (PBL) which can be decorated with a wide range of decorations to improve the aesthetic appearance of the product, especially cosmetic products. All layers of the packaging can be made using standard manufacturing methods including, but not limited to, lamination, extrusion, blow molding, and/or injection molding.

The first composition is provided in the outer tube interior chamber 60 and the second composition is provided in the inner tube interior chamber 80.

| Example | Exterior layer of outer tube - material | Exterior layer of outer tube- thickness (um) | Exterior layer of outer tube- Stiffness (N) |
| --- | --- | --- | --- |
| Example 1 | PBL | 350 | 3.645 |
| Example 3 | Mono LDPE | 450 | 3.1 |
| Comparative B | PBL | 350 | 3.645 |
| Example 4 | PBL | 350 | 3.645 |
| Comparative C | PBL | 350 | 3.645 |
| Comparative D | PBL | 425 | 5.61 |

| Example | Exterior layer of inner tube - material | Exterior layer of inner tube- thickness (um) | Exterior layer of inner tube- Stiffness (N) |
| --- | --- | --- | --- |
| Example 1 | Mono LDPE | 450 | 4.463 |
| Example 3 | Mono LDPE | 450 | 4.463 |

| Example | Exterior layer of inner tube - material | Exterior layer of inner tube- thickness (um) | Exterior layer of inner tube- Stiffness (N) |
|---|---|---|---|
| Comparative B | 100% PP | 450 | 9.230 |
| Example 4 | 50% HD + 50% LD | 450 | 9.176 |
| Comparative C | 100% HD | 450 | 9.610 |
| Comparative D | Mono LDPE | 450 | 4.463 |

| Example | Stiffness ratio of outer tube exterior layer and inner tube exterior layer | Dispense ratio | Dispense ratio std. |
|---|---|---|---|
| Example 1 | 0.8167 | 0.7263 | 0.0650 |
| Example 3 | 0.6946 | 0.4895 | 0.0637 |
| Comparative B | 0.3949 | 0.4393 | 0.1045 |
| Example 4 | 0.3972 | 0.4983 | 0.0304 |
| Comparative C | 0.3793 | 0.4532 | 0.0525 |
| Comparative D | 1.2570 | 0.4102 | 0.0526 |

Test Methods

Tube Stiffness

Tube Stiffness is measure using the Standard Test Method for Determination of External Loading Characteristics of Plastic Pipe by Parallel-Plate Loading ASTM Designation: D 2412-02 (Reapproved 2008). All test specimen are standardized to be 100 mm long, and deflect to 50% of the tube diameter, and peak squeeze force is recorded.

G' Modulus Pa

The Oscillatory Rheometry Test Method is used to determine the crossover stress and storage modulus of a gel-like/semisolid product (the G' Modulus Values in Pa units).

A controlled-stress rotational rheometer (such as Discovery HR-2, TA Instruments, New Castle, Del., USA, or equivalent) capable of sample temperature control (using a Peltier cooler and resistance heater combination) is used for the test.

The rheometer is operated in a parallel plate configuration with 40-mm crosshatch stainless steel parallel-plate tooling. The rheometer is set at 25° C. Approximately 2 ml of sample is gently loaded onto peltier plate using a spatula from the sample jar without any shear to change the product structure, and excess protruding sample is trimmed once the gap reached 1000 m after sample loading. Sample is then equilibrated at 25° C. for 120 seconds before measurement starts. For different rheometer, extend the equilibrium time to ensure the sample temperature achieved 25° C. before the test. The test commences with rheometer increased from strain amplitude 0.1% to 1000% in logarithmic mode with oscillation frequency fixed at 1 Hz (that is, one cycle per second) at 25° C.

For each strain amplitude sampled, the resulting time-dependent stress is analyzed according to the customary linear oscillatory strain formalism, known to those of skill in the art, to obtain the storage modulus (G') and loss modulus (G") at each step. A plot is made in which G' and G" (both expressed in units of Pascals, vertical axis) are plotted versus the strain amplitude (percent strain, horizontal axis). The lowest strain amplitude at which the traces for G' and G" cross (that is, when $\tan(\delta)=G"/G'=1$) is recorded, and the value of G' and G" at this point is defined as the crossover stress and is reported in units of Pa.

Rheological properties measured by the rheometer provided by the present disclosure include, but are not limited to, storage modulus G', a loss modulus G", loss factor $\tan(\delta)$. Crossover point, is extracted using TRIOS software (provided by TA instrument) and is applicable for other equivalent rheology software.

Dispense Method

Measuring the ratio of dispensed first and second compositions is measured using the following method:
1. Hold the tube in a vertical position (FIG. 4).
2. Dispense about 10 g of product from tube on a weigh scale (FIG. 5).
3. Use a spatula to scoop the outer phase and measure the remaining inner phase product left on the weigh scale (FIGS. 6 and 7).
4. Continue to dispense the tube with every 10 g until tube is empty.
5. For each dispense, the ratio of the outer to inner phase product is determined.
6. The ratios for each tube are analyzed for mean and standard deviation of the mean.

Figure 4:
FIG. 4 is a demonstration of dispensing product for a test method.
Figure 5:
FIG. 5 is a demonstration of dispensing product for a test method.
Figure 6:
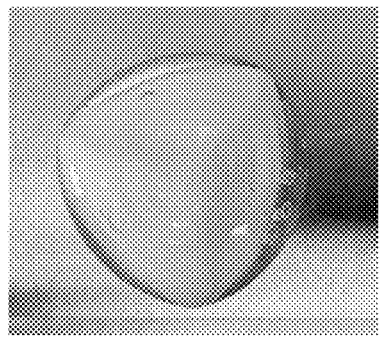
FIG. 6 is product dispensed for a test method.
Figure 7:
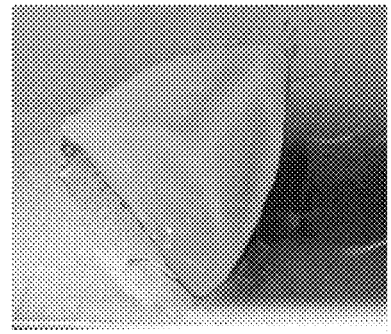
FIG. 7 is product dispensed for a test method.

FIG. 4. Maintain the tube in a vertical position.
FIG. 5. Dispense around 10 g of product on weigh scale while maintaining the vertical position of the tube.
FIG. 6 shows the product before scooping off the outer phase, and FIG. 7 shows the product after scooping off the outer phase product.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A packaged hair care composition comprising
a hair care composition comprising:
a first composition and a second composition,
wherein the first and second compositions are kept separate from one another until dispensed,
wherein the first composition comprises: a cationic polymer; and an aqueous carrier and has a G' value of about 160 to about 410; and
wherein the second composition comprises: a cationic surfactant; a high melting point fatty compound; and an aqueous carrier and has a G' value of from about 600 Pa to about 3000 Pa
a package comprising:
an outer tube body having an exterior layer wherein the outer tube exterior layer has a stiffness of from about 3.0 N to about 9.5 N and a thickness of from about 300 μm to about 600 μm and an outer tube interior chamber; and an inner tube having an exterior layer wherein the interior tube exterior layer has a stiffness of from about 2.9 N to about 9.5 N and a thickness of from about 200 μm to about 600 μm and an inner tube body having an inner tube interior chamber;

a dispensing orifice wherein a portion of the dispensing orifice is in communication with the outer tube interior chamber, and a portion of the dispensing orifice is in communication with the inner tube interior chamber;

wherein the first composition is located in the outer tube interior chamber, and the second composition is located in the inner tube interior chamber.

2. The packaged hair care composition claim 1, wherein the first composition has a G' value of from about 175 Pa to about 390 Pa.

3. The packaged hair care composition of claim 2, wherein the first composition has a G' value of from about 190 Pa to about 370 Pa.

4. The packaged hair care composition of claim 1, wherein the second composition has a G' value of from about 650 Pa to about 2700 Pa.

5. The packaged hair care composition of claim 4, wherein the second composition has a G' value of from about 700 Pa to about 2300 Pa.

6. The packaged hair care composition of claim 1, wherein the outer tube exterior layer has a stiffness of from about 3.0 N to about 5.5 N.

7. The packaged hair care composition of claim 6, wherein the outer tube exterior layer has a stiffness of from about 3.2 N to about 4.0 N.

8. The packaged hair care composition of claim 1, wherein the outer tube exterior layer has a thickness of from about 300 μm to about 500 μm.

9. The packaged hair care composition of claim 8, wherein the outer tube exterior layer has a thickness of from about 300 μm to about 400 μm.

10. The packaged hair care composition of claim 1, wherein the inner tube exterior layer has a stiffness of from about 3.0 N to about 6.0 N.

11. The packaged hair care composition of claim 10, wherein the inner tube exterior layer has a stiffness of from about 4.0 N to about 5.0 N.

12. The packaged hair care composition of claim 1, wherein the stiffness ratio of the exterior layer of the outer tube to the exterior layer of the inner tube is from about 0.35 to about 1.2.

13. The packaged hair care composition of claim 12, wherein the stiffness ratio of the exterior layer of the outer tube to the exterior layer of the inner tube is from about 0.6 to about 1.2.

14. The packaged hair care composition of claim 13, wherein the stiffness ratio of the exterior layer of the outer tube to the exterior layer of the inner tube is from about 0.7 to about 1.0.

15. The packaged hair care composition of claim 1, wherein the outer tube exterior layer comprises a material selected from the group consisting of plastic laminate, metallized laminate, aluminum laminate, polypropylene, and combinations thereof.

16. The packaged hair care composition of claim 1, wherein the inner tube exterior layer comprises a material selected from the group consisting of plastic laminate, metallized laminate, aluminum laminate, polypropylene, and combinations thereof.

17. The packaged hair care composition of claim 1, wherein the cationic polymer is polyquaternium-37.

18. The packaged hair care composition of claim 1, wherein the second composition comprises a silicone compound.

19. The packaged hair care composition of claim 18, wherein the silicone compound conforms to the general formula:

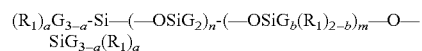

wherein G is hydrogen, phenyl, hydroxy, or $C_1$-$C_8$ alkyl, preferably methyl; a is 0 or an integer having a value from 1 to 3; b is 0, 1 or 2; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$$A^-$; —N($R_2$)$CH_2$—$CH_2$—$NR_2H_2A^-$; wherein $R_2$ is hydrogen, phenyl, benzyl, or a saturated hydrocarbon radical; $A^-$ is a halide ion.

20. The packaged hair care composition of claim 1, wherein the first composition and the second composition are mixed at a G' ratio of from about 0.10 to about 0.40.

21. The packaged hair care composition of claim 20, wherein the first composition and the second composition are mixed at a G' ratio of from about 0.11 to about 0.35.

22. The packaged hair care composition of claim 20, wherein the first composition and the second composition are mixed at a G' ratio of from about 0.13 to about 0.30.

23. The packaged hair care composition of claim 1, wherein less than 12.5 weight % of the first and second composition remain in the package after the product has been dispensed during use.

* * * * *